US009767591B2

United States Patent
Seo et al.

(10) Patent No.: US 9,767,591 B2
(45) Date of Patent: *Sep. 19, 2017

(54) METHOD AND APPARATUS FOR PROVIDING BIOMETRIC INFORMATION

(71) Applicant: Samsung Electronics Co., Ltd., Gyeonggi-do (KR)

(72) Inventors: Hyung-jin Seo, Gyeonggi-do (KR); Jae-young Lee, Gyeonggi-do (KR); Sung-hyun Cho, Seoul (KR); Cory Kim, Gyeonggi-do (KR); Jong-eun Yang, Seoul (KR)

(73) Assignee: Samsung Electronics Co., Ltd (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/921,730

(22) Filed: Oct. 23, 2015

(65) Prior Publication Data

US 2016/0048990 A1    Feb. 18, 2016

Related U.S. Application Data

(63) Continuation-in-part of application No. 14/920,531, filed on Oct. 22, 2015, which is a continuation of application No. 12/871,291, filed on Aug. 30, 2010, now Pat. No. 9,183,356.

(30) Foreign Application Priority Data

Aug. 28, 2009  (KR) ........................ 10-2009-0080723

(51) Int. Cl.
*G06F 19/00*   (2011.01)
*G06T 11/00*   (2006.01)
(Continued)

(52) U.S. Cl.
CPC .............. *G06T 11/60* (2013.01); *A61B 5/021* (2013.01); *A61B 5/4509* (2013.01);
(Continued)

(58) Field of Classification Search
None
See application file for complete search history.

(56) References Cited

U.S. PATENT DOCUMENTS

| 5,546,943 A | 8/1996 | Gould |
| 6,839,455 B2 | 1/2005 | Kaufman |

(Continued)

FOREIGN PATENT DOCUMENTS

| JP | 2004008659 | 1/2004 |
| JP | 2004041811 | 2/2004 |

(Continued)

OTHER PUBLICATIONS

Korean Office Action dated Sep. 18, 2015 issued in counterpart application No. 10-2009-80723, 11 pages.

*Primary Examiner* — Andrew G Yang
(74) *Attorney, Agent, or Firm* — The Farrell Law Firm, P.C.

(57) ABSTRACT

An apparatus and a method for providing information are provided. The apparatus includes an interfacing unit configured to receive biometric information, which is measured by an external measuring device, corresponding to a health condition of a body part of a user, from the external measuring device; and a processor configured to determine a visual metaphor representation for characterizing a degree of the health condition based on mapping information between components of the visual metaphor representation and types of the received biometric information, and transform the received biometric information into the determined visual metaphor representation, where the interfacing unit is configured to transmit the transformed visual metaphor representation to an external displaying device.

10 Claims, 17 Drawing Sheets

(51) Int. Cl.
*G06T 11/60* (2006.01)
*A61B 5/00* (2006.01)
*A61B 5/021* (2006.01)
*G09G 5/00* (2006.01)

(52) U.S. Cl.
CPC ............ *A61B 5/4866* (2013.01); *A61B 5/742* (2013.01); *G06F 19/321* (2013.01); *G06F 19/345* (2013.01); *G06F 19/3487* (2013.01); *G09G 5/00* (2013.01); *G09G 2340/14* (2013.01)

(56) References Cited

U.S. PATENT DOCUMENTS

| | | | |
|---|---|---|---|
| 8,463,006 | B2 | 6/2013 | Prokoski |
| 9,101,261 | B2 | 8/2015 | Kim et al. |
| 2003/0217294 | A1 | 11/2003 | Kyle |
| 2005/0222638 | A1 | 10/2005 | Foley et al. |
| 2006/0178661 | A1 | 8/2006 | Neher et al. |
| 2009/0009284 | A1 | 1/2009 | Sako |
| 2009/0024415 | A1 | 1/2009 | Alpert et al. |
| 2009/0148020 | A1 | 6/2009 | Sugiura |
| 2009/0175491 | A1 | 7/2009 | Charpentier |
| 2009/0306511 | A1 | 12/2009 | Yamagata |
| 2010/0204616 | A1 | 8/2010 | Shears et al. |

FOREIGN PATENT DOCUMENTS

| | | |
|---|---|---|
| JP | 2008131977 | 6/2008 |
| KR | 10-2006-0032409 | 4/2006 |

FIG. 2
[BONE DENSITY]
| MEASURED BODY PART | DISPLAY |
|---|---|
| FINGERS | 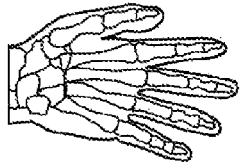 |
| ARM |  |
| RIBS | 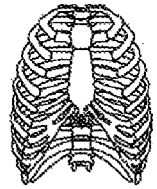 |
FIG. 3
[BONE DENSITY]
| MEASURED BODY PART | DISPLAY |
|---|---|
| FINGERS |  |
| ARM |  |
| RIBS |  |

| BLOOD PRESSURE | STRENGTH | TEMPERATURE |
|---|---|---|
| 150~ | 3 | 20 |
| 120~140 | 2 | 25 |
| 100~120 | 1 | 30 |

|  | AIRPLANE | PLANT | TRAFFIC LIGHT |
|---|---|---|---|
| BONE DENSITY | RIGHT WING | STEMS | RED LIGHT |
| BLOOD PRESSURE | LEFT WING | LEAVES | ORANGE LIGHT |
| OBESITY LEVEL | PROPELLAR | FRUITS | BLUE LIGHT |

METHOD AND APPARATUS FOR PROVIDING BIOMETRIC INFORMATION

PRIORITY

This application is a continuation-in-part of U.S. patent application Ser. No. 14/920,531, filed on Oct. 22, 2015, which is a continuation of U.S. patent application Ser. No. 12/871,291, filed on Aug. 30, 2010, and which claims priority under 35 U.S.C. §119(a) to Korean Patent Application No. 10-2009-0080723, filed on Aug. 28, 2009, in the Korean Intellectual Property Office, the entire content of which is incorporated herein by reference.

BACKGROUND OF THE INVENTION

1. Field of the Invention

The present invention relates generally to a method and apparatus for providing information, and more particularly, to a method and apparatus for providing biometric information.

2. Description of the Related Art

As the number of people in poverty has been significantly decreasing and standards of living have been increasing, interest in health has been increasing. Accordingly, measurement and management of physical health status has become increasingly commonplace, regardless of age.

In particular, older people periodically measure their physical health status through health screening and understand their physical health status by examining numerical data.

SUMMARY OF THE INVENTION

The present invention provides a method and apparatus for effectively providing biometric information.

According to an aspect of the present invention, an apparatus for providing information is provided. The apparatus includes an interfacing unit configured to receive biometric information, which is measured by an external measuring device, corresponding to a health condition of a body part of a user, from the external measuring device; and a processor configured to determine a visual metaphor representation for characterizing a degree of the health condition based on mapping information between components of the visual metaphor representation and types of the received biometric information, and transform the received biometric information into the determined visual metaphor representation, where the interfacing unit is configured to transmit the transformed visual metaphor representation to an external displaying device.

According to another aspect of the present invention, a method for providing information at information providing apparatus is provided. The method includes receiving biometric information, which is measured by an external measuring device, corresponding to a health condition of a body part of a user, from the external measuring device, determining a visual metaphor representation for characterizing a degree of the health condition based on mapping information between components of the visual metaphor representation and types of the received biometric information, transforming the received biometric information into the determined visual metaphor representation, and transmitting the transformed visual metaphor representation to an external displaying device.

BRIEF DESCRIPTION OF THE DRAWINGS

The above and other features and advantages of the present invention will become more apparent by describing in detail embodiments thereof with reference to the attached drawings in which:

FIG. 2 is a table used by the apparatus of FIG. 1 to process biometric information, according to an embodiment of the present invention;

FIG. 3 is a table used by the apparatus of FIG. 1 to process biometric information, according to another embodiment of the present invention;

DETAILED DESCRIPTION OF THE INVENTION

The present invention will now be described more fully with reference to the accompanying drawings, in which embodiments of the invention are shown.

Figure 1:
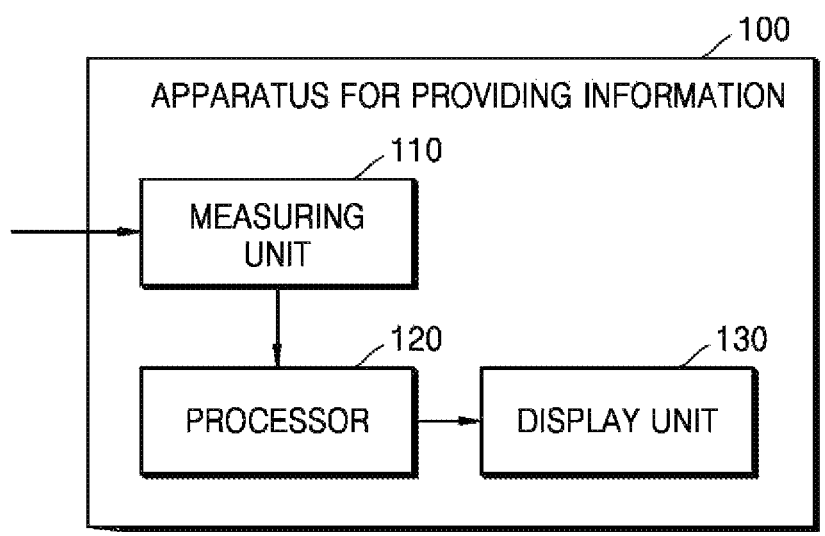
FIG. 1 is a block diagram of an apparatus for providing information, according to an embodiment of the present invention.

FIG. 1 is a block diagram of an apparatus 100 for providing information, according to an embodiment of the present invention.

Referring to FIG. 1, the apparatus 100 includes a measuring unit 110, a processor 120, and a display unit 130. The measuring unit 110 measures biometric information of a user. The biometric information may include any information about a user's body. For example, the biometric information may include at least one information item selected from a group including of blood pressure, pulse, electrocardiogram, heart rate, skin surface temperature, respiratory amount, weight, height, body movement, electromyogram, perspiration, and skin response.

The measuring unit 110 may further acquire information about a measured body part, the biometric information of which has been measured. For example, if blood pressure is measured by attaching a sensor to one of the arms of the user, blood pressure information is used as the biometric information, while the arm is the measured body part.

The processor 120 processes the biometric information. The biometric information measured by the measuring unit 110 is generally expressed through numerical data. The processor 120 enables the user to intuitively understand the biometric information expressed using the numerical data by transforming the numerical data into another form, such as sight, hearing, or touch.

The processor 120 may process the biometric information based on a type of the biometric information. If the biometric information is blood pressure, the processor 120 may visualize the blood pressure as veins and express the measurement of the blood pressure by using a degree of expansion or color of the veins. If the blood pressure is expressed using numerical data, the user may not intuitively understand the status of the blood pressure. However, if the blood pressure is expressed using a degree of expansion or color of the veins, the user may intuitively understand the status of the blood pressure.

The processor 120 may process the biometric information based on the measured body part. For example, if bone density is measured by attaching sensors to the fingers of the user, since the measured body part is the fingers, the processor 120 may visualize the bone density as finger bones. Likewise, if bone density is measured by attaching the sensor to the chest, since the measured body part is the chest, the processor 120 may visualize the bone density as ribs.

The processor 120 may also process the biometric information further based on profile information of the user. The profile information of the user may include any information related to the user, including, age, occupation, mental age, height, and family relationships. Accordingly, the processor 120 may change an object as which the biometric information is visualized based on the profile information of the user. For example, such an object change may occur for children, who may be repulsed by visualizations of finger bones or veins, as described above.

The processor 120 may process the biometric information so that the user may understand the biometric information by using sight, touch, hearing, or smell. A method of processing the biometric information to transfer the biometric information to the user by using touch is described herein with reference to FIG. 6.

The display unit 130 may display the biometric information on the measured body part. For example, if the measured body part is one of the hands of the user, the display unit 130 may display finger bones on a surface of the hand of the user or on the sensor by using a laser or a projector.

The display unit 130 displays the biometric information over image data obtained by photographing the measured body part. The display unit 130 may combine the image data corresponding with the measured body part with the biometric information to generate new image data, or may overlap the biometric information and the image data by using a laser or a projector.

If several pieces of image data are obtained by photographing the measured body part, a signal for selecting one of the several pieces of image data on which the biometric information is to be displayed may be received through an interface.

The apparatus 100 may further include a transmitting unit (not shown) or a receiving unit (not shown).

The receiving unit receives the image data from an external device connected through a network to the apparatus 100. The apparatus 100 may be connected through a wired network, such as Local Area Network (LAN), or a wireless network, such as High-Speed Downlink Packet Access (HSDPA) or WIreless BROadband (WiBro), to at least one external device (not shown).

The transmitting unit transmits the image data on which the biometric information processed by the processor 120 has been displayed to the external device through the network. The user may receive the transmitted image data through a receiving device, such as a computer or a mobile phone, and understand his/her health status by using the receiving device.

FIG. 2 is a table used by the apparatus 100 of FIG. 1 to process the biometric information, according to an embodiment of the present invention.

Referring to FIGS. 1 and 2, when bone density of the user is measured as biometric information, the processor 120 visualizes the bone density as bones so that the user may see and intuitively understand the status of his/her bone density. At this time, the processor 120 may change a color of the bones in order to indicate whether numerical data of the bone density is normal or abnormal.

The processor 120 may determine a type of bones to be visualized according to a measured body part, the bone density of which has been measured. For example, the processor 120 visualizes the bone density as finger bones if the bone density is measured by attaching the sensor to one of the hands of the user, the processor 120 visualizes the bone density as arm bones if the bone density is measured by attaching the sensor to one of the arms of the user, and the processor 120 visualizes the bone density as ribs if the bone density is measured by attaching the sensor to the chest of the user.

FIG. 3 is a table used by the apparatus 100 of FIG. 1 to process the biometric information, according to another embodiment of the present invention.

Referring to FIG. 3, bone density of the user is also measured. However, in FIG. 3, an object as which the bone density is visualized is changed in consideration of the age of the user. For example, if the user is a child or another person who may feel repulsed by a visualization of a body part, the user may not prefer images of bones for a bone density visualization. In such a case, the processor 120 may visualize bone density as something that is not repulsive to the user.

Referring to the table of FIG. 3, if the measured body part includes fingers, for example, the bone density may be visualized as veins of a leaf, and if the measured body part is one of the arms, the bone density may be visualized as a log. Also, if the measured body part is ribs, the bone density may be visualized as umbrella ribs.

Bone density may be measured by attaching a sensor to a user's arm. If the bone density is normal, the bone density may be visualized as a solid log, and if the bone density is abnormal, the bone density may be visualized as a log with a hole. If the measured bone density value is much less than a normal bone density value, the measured bone density may be visualized as a log having lots of holes, so that the user may intuitively understand his/her status.

Figure 4:
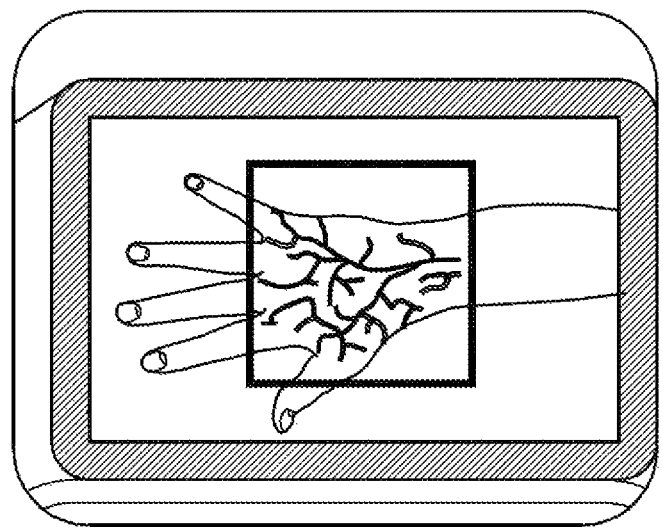
FIG. 4 is an example of an image displayed by the apparatus of FIG. 1, according to an embodiment of the present invention.

FIG. 4 is an example of an image displayed by the apparatus 100 of FIG. 1, according to an embodiment of the present invention.

Referring to FIG. 4, blood pressure may be measured by attaching a sensor a hand of the user. Accordingly, in this example, the hand is the measured body part and blood pressure is the biometric information.

The processor 120 visualizes the blood pressure as veins. If the measured blood pressure is high, the processor 120 visualizes the blood pressure as veins that are greatly expanded. However, if the measured blood pressure of the user is a normal value, the processor 120 visualizes the blood pressure as veins that are not expanded.

The display unit 130 directly displays the biometric information, which has been processed by the processor 120, on the hand of the user by using the projector. More specifically, the display unit 130 displays the veins on the hand of the user. The user may intuitively understand the status of his/her blood pressure by checking whether the veins visualized on the user's hand are expanded.

Figure 5:
FIG. 5 is an example of another image displayed by the apparatus of FIG. 1, according to another embodiment of the present invention.

FIG. 5 is an example of another image displayed by the apparatus 100 of FIG. 1, according to another embodiment of the present invention.

Referring to FIG. 5, a status of a user's teeth is measured by an X-ray. Accordingly, in this example, the teeth are the measured body part, and the status of the teeth the biometric information.

The processor 120 visualizes the status of the teeth as a worm. When, a status of the teeth is worse than the example depicted in FIG. 5, a larger worm or a greater number of worms may be displayed, so that a user may intuitively understand the status of his/her teeth.

The display unit 130 displays the biometric information, which has been processed by the processor 120, on an X-ray image obtained by photographing the user's teeth.

If the status of the teeth of the user is unhealthy, for example, if there is a decayed tooth or the teeth are not well taken care of, a worm may be added to the X-ray image of the teeth.

However, if the status of the teeth of the user is healthy, for example, if there are no decayed tooth and the teeth are well taken care of, a message indicating that the teeth are healthy may be displayed by on the X-ray image of the teeth.

Figures 6, 7:
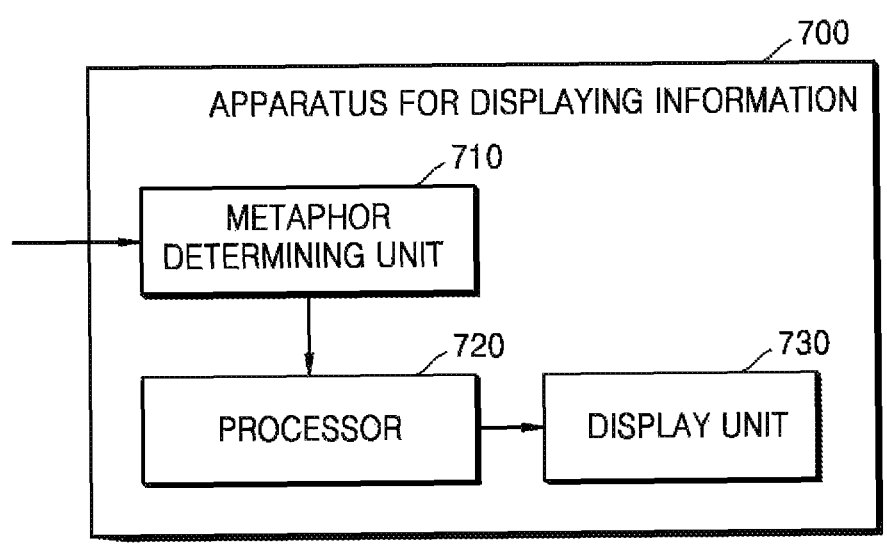
FIG. 6 is a table used by the apparatus of FIG. 1 to display biometric information, according to an embodiment of the present invention.
FIG. 7 is a block diagram of an apparatus for providing information, according to another embodiment of the present invention.

FIG. 6 is a table used by the apparatus 100 of FIG. 1 to display the biometric information in a case where the apparatus 100 transfers the biometric information to the user by using a touch according to an embodiment of the present invention.

Referring to FIGS. 1 and 6, the apparatus 100 measures blood pressure by attaching a sensor to an arm of a user, and displays an indication of blood pressure according to a change in temperature and pressure applied to the arm.

If the blood pressure of the user ranges from 100 to 120, no stimulus or only a weak stimulus may be applied to the arm of the user. When no stimulus or only a weak stimulus is applied to the arm of the user, the user may intuitively understand that his/her blood pressure is normal.

However, if the blood pressure of the user ranges from 120 to 140, a stimulus having twice a magnitude as the stimulus applied when the blood pressure is normal is applied to the user's arm and a temperature of the sensor is reduced to 25° C. The user may intuitively understand that his/her blood pressure is abnormal by recognizing that the temperature of the sensor has changed.

If the blood pressure of the user is greater than 150, a stimulus having three times the magnitude of the stimulus applied when the blood pressure is normal is applied to the arm of the user and the temperature of the sensor is reduced to a temperature lower than 20° C. The user can understand that his/her blood pressure is dangerous by recognizing that a stimulus applied to the arm of the user is large and recognizing that the arm is cooled by the temperature sensor.

FIG. 7 is a block diagram of an apparatus 700 for providing information, according to another embodiment of the present invention.

Referring to FIG. 7, the apparatus 700 includes a metaphor determining unit 710, a processor 720, and a display unit 730.

The metaphor determining unit 710 determines a metaphor through which biometric information is visualized. The metaphor determining unit 710 may display a metaphor list to the user and the user may select an item in the metaphor list.

The processor 720 visualizes the biometric information of the user as at least one component of the metaphor. The processor 720 may visualize the biometric information based on mapping information between the biometric information and the components of the metaphor. The mapping information between the biometric information and the components of the metaphor are described herein below with reference to FIG. 8.

The display unit 730 displays the biometric information that has been visualized by the processor 720.

Figures 8, 9:
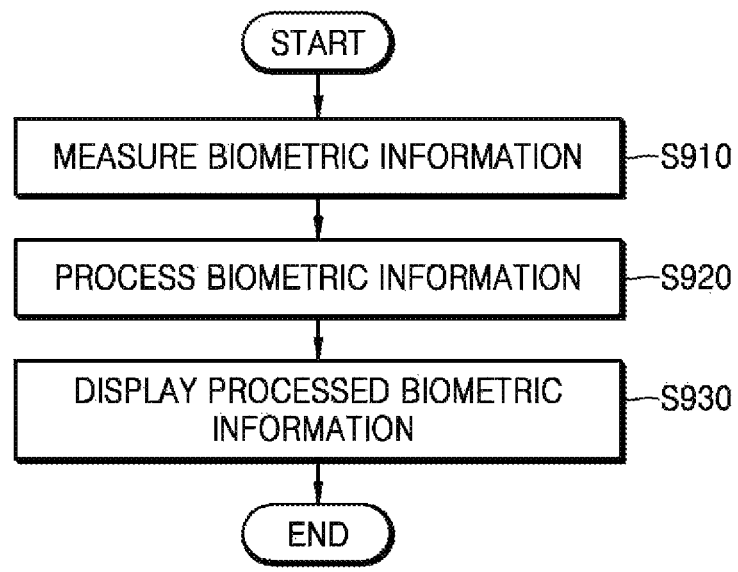
FIG. 8 is a table used by the apparatus of FIG. 7 to display biometric information.
FIG. 9 is a flowchart illustrating a method of providing information, according to an embodiment of the present invention.

FIG. 8 illustrates a mapping table between the biometric information and the metaphor used by the apparatus 700 of FIG. 7 to display the biometric information, according to an embodiment of the present invention.

For example, a user may select one of an airplane, a plant, and a traffic light as the metaphor. If the user selects the airplane as the metaphor, bone density may be displayed as a right wing of the airplane, blood pressure may be displayed as a left wing of the airplane, and obesity level may be displayed as a propeller. If the bone density is abnormal, the apparatus 100 may display the airplane as if smoke is rising up from the right wing of the airplane. The apparatus 100 may display more smoke rising up from the right wing as the bone density worsens.

If the user selects the plant as the metaphor, the bone density of the user may be displayed as stems, the blood pressure of the user may be displayed as leaves, and the obesity level of the user may be displayed as fruits. For example, if the blood pressure is abnormal, the apparatus 100 may display the plant as if the leaves of the plant are dry and drooping downwards. In particular, the apparatus 100 may display a greater number of leaves drooping downwards as the blood pressure worsens.

If the user selects the traffic light as the metaphor, the bone density of the user may be displayed as a red light, the blood pressure of the user may be displayed an orange light, and the obesity level of the user may be displayed as a blue light. For example, if the obesity level of the user is abnormal, the apparatus 100 may reduce the displayed intensity of the traffic light. More specifically, the apparatus 100 may reduce the displayed intensity of the traffic light as the obesity level of the user worsens.

FIG. 9 is a flowchart illustrating a method of providing information, according to an embodiment of the present invention.

In step S910, biometric information of a user is measured.

In step S920, the biometric information is processed based on at least one item selected from a group including a type of the biometric information, a measured body part, the biometric information of which has been measured, and a profile of the user.

In step S930, the biometric information is displayed on the measured body part or the biometric information is added to image data obtained by photographing the measured body part. If a plurality of pieces of image data is obtained by photographing the measured body part, one piece of the obtained image data on which the biometric information is to be displayed may be selected. The image data to which the biometric information is added may be transmitted to an external device through a network, and the user may directly understand the biometric information by using the external device. The user may understand the biometric information by using sight, hearing, or touch.

Figure 10:
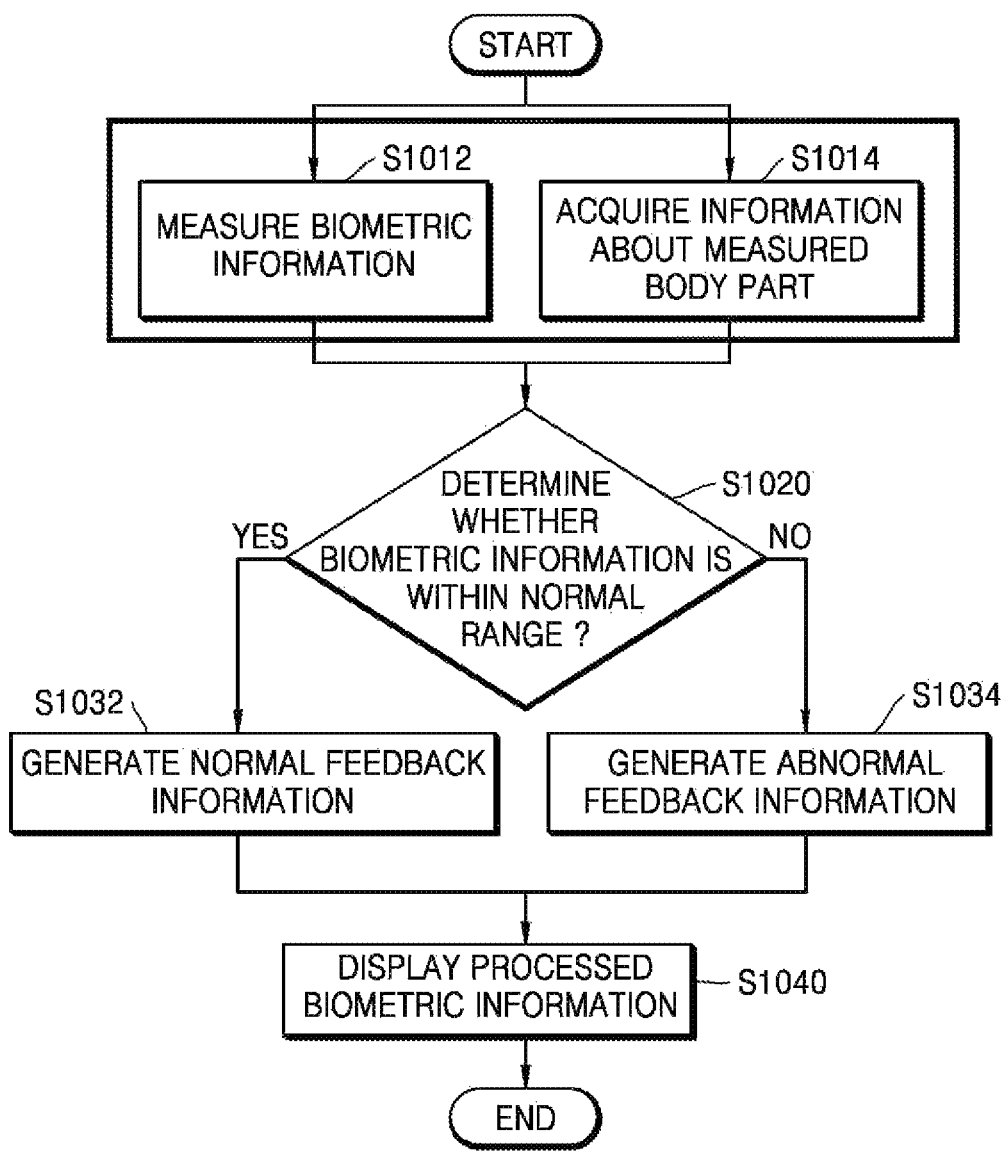
FIG. 10 is a flowchart illustrating a method of providing information, according to another embodiment of the present invention.

FIG. 10 is a flowchart illustrating a method of providing biometric information to a user, according to another embodiment of the present invention.

Referring to FIG. 10, in step S1012, biometric information of a user is measured. In step S1014, information about a measured body part, the biometric information of which has been measured, is acquired. In step S1020, it is determined whether the biometric information is within a normal range. If the biometric information is within the normal range, the method proceeds to step S1032. Otherwise, the method proceeds to step S1034.

In step S1032, the biometric information is processed so that the user may intuitively know that the biometric information is normal. In step S1034, the biometric information is processed so that the user may intuitively know that the biometric information is abnormal. In step S1040, the processed biometric information is displayed.

Figure 11:
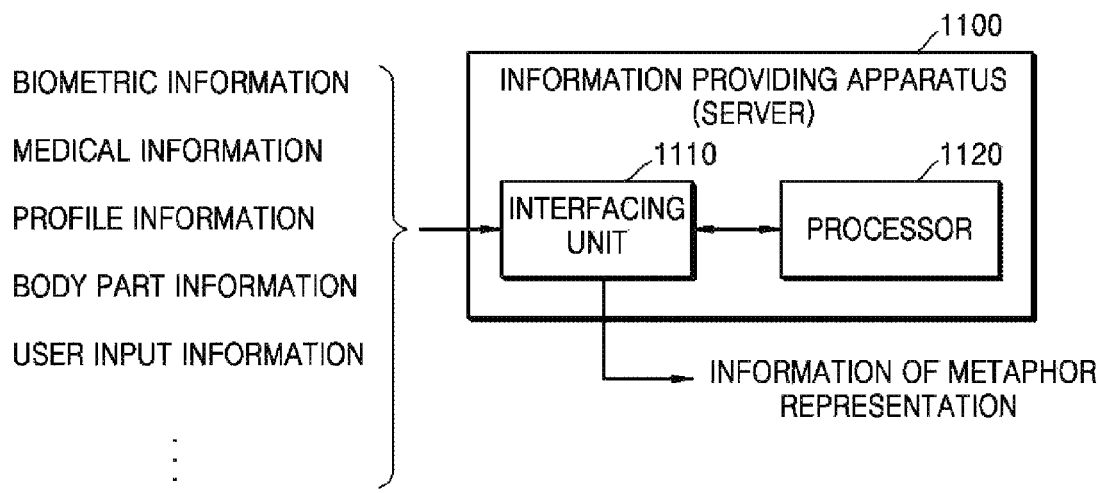
FIG. 11 is a block diagram of an apparatus for providing information, according to another embodiment of the present invention.

FIG. 11 is a block diagram of an apparatus for providing information, according to another embodiment of the present invention.

Referring to FIG. 11, the apparatus 1100 includes an interfacing unit 1110 and a processor 1120. That is, the apparatus 1100 does not include the measuring unit 110 and the display unit 130, unlike the apparatus 100 of FIG. 1 and the apparatus 700 of FIG. 7. The apparatus 1100 may correspond to a server.

The interfacing unit 1110 receives biometric information, medical information, profile information, body part information, and user input information from the outside. The interfacing unit 1110 corresponds to hardware configured to enable the apparatus 1100 to receive data from the outside or to transmit data to the outside.

The processor 1120 corresponds to hardware configured to perform functions similar to those of the processor 120 of FIG. 1 or the metaphor determining unit 710 and the processor 720 of FIG. 7. Accordingly, the processor 1120 may perform the same operations as those of the processor 120, the metaphor determining unit 710, and the processor 720.

The processor 1120 processes the biometric information, the medical information, the profile information, the body part information, or the user input information received through the interfacing unit 1110. The biometric information, the profile information, and the body part information have already been explained. The processor 1120 may determine a visual metaphor representation, and may generate an image in which the determined visual metaphor representation is reflected, like the processor 120 of FIG. 1 or the metaphor determine 710 and the processor 720 of FIG. 7. That is, the processor 1120 may process the biometric information as a metaphor representation by using the methods of FIGS. 1 through 10. The medical information may be information about medical records of a patient that is stored in a server run by a hospital or another medical institution.

The interfacing unit 1110 may transmit the information of the metaphor representation processed by the processor 1120 to the outside.

Figure 12:
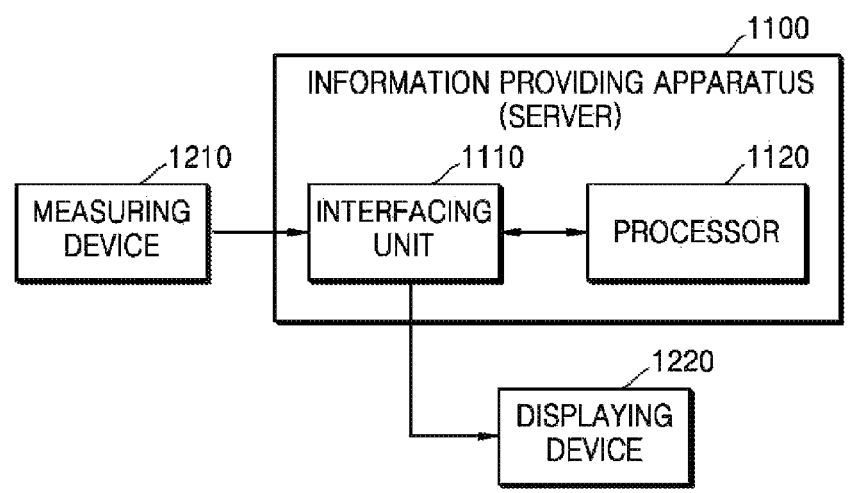
FIG. 12 is a block diagram of an apparatus for providing information, according to another embodiment of the present invention.

FIG. 12 is a block diagram of an apparatus for providing information, according to another embodiment of the present invention.

Referring to FIG. 12, the apparatus 1100 includes the interfacing unit 1110 and the processor 1120. Unlike the apparatus 100 of FIG. 1 and the apparatus 700 of FIG. 7, the apparatus 1100 does not include the measuring unit 110 and the display unit 120. However, the apparatus 1100 may receive biometric information, medical information, and user input information from an external measuring device 1210, may process the biometric information, the medical information, and the user input information, and may transmit a processing result (e.g., information of a metaphor representation) to an external displaying device 1220. That is, the apparatus 1100 may be a hardware apparatus that functions as a server for processing the biometric information between the measuring device 1210 and the displaying device 1220.

Examples of the measuring device 1210 for measuring biometric information may include a smart phone, a wearable device, an augmented reality (AR) device, a virtual reality (VR) device, a smart mirror, and other bioelectrical measuring units.

The measuring device 1210 measures biometric information of a user. The biometric information may include any information related to the user's body. For example, the biometric information may include blood pressure, pulse, electrocardiogram, electroencephalogram, heart rate, skin surface temperature, respiratory amount, weight, height, body movement, electromyogram, perspiration, stress level, bone mineral density, body mass index information, calories burned information, physical age, and skin response. The measuring device 1210 may further obtain information about a measured body part, the biometric information of which has been measured. If blood pressure is measured by attaching a sensor to one of the arms of the user, blood pressure information corresponds to the biometric information and the arm corresponds to the measured body part.

The measuring device 1210 may provide the measured biometric information to the apparatus 1100. Also, the measuring device 1210 may provide profile information, body part information, and user input information to the apparatus 1100. The measuring device 1210 may be a server run by a hospital or another medical institution, and in this case, the measuring device 1210 may provide information about medical records of a patient to the apparatus 1100.

Examples of the displaying device 1220 for displaying information of a metaphor representation transmitted from the apparatus 1100 may include a smart phone, a wearable device, an AR device, a VR device, a smart mirror, and any device including a display screen.

The interfacing unit 1110 of the apparatus 1100 receives the biometric information, the medical information, the profile information, the body part information, and the user input information from the measuring device 1210. The interfacing unit 1110 of the apparatus 1100 transmits the information of the metaphor representation to the displaying device 1220.

The processor 1120 of the apparatus 1100 may process the biometric information by using sight, hearing, or touch so that the user intuitively understands the biometric information, may process the biometric information based on a type of the biometric information, or may process the biometric information based on a body part, like the processor 120 of FIG. 1 or the metaphor determining unit 710 and the processor 720 of FIG. 7. Also, the processor 1120 may process the biometric information further based on the profile information. Also, the processor 1120 may determine a metaphor through which the biometric information is visualized, and may visualize the biometric information as one or more components constituting the metaphor. The processor 1120 may transmit the information of the visual metaphor representation corresponding to the processed biometric information to the interfacing unit 1110. The processor 1120 may generate an image in which the biometric information overlaps the photographed body part. In this case, the processor 1120 may generate an image in which the visual metaphor representation corresponding to the processed biometric information is reflected, and the processor 1120 may transmit the generated image to the interfacing unit 1110. That is, the processor 1120 may process the biometric information as the metaphor representation by using the methods of FIGS. 1 through 10.

Figure 13:
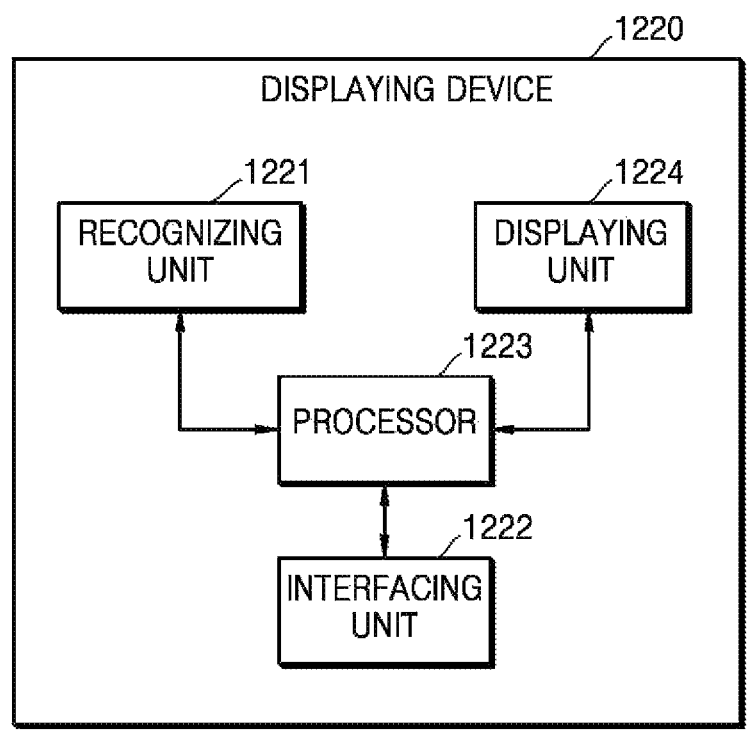
FIG. 13 is a block diagram of the displaying device of FIG. 12, according to an embodiment of the present invention.

FIG. 13 is a block diagram of the displaying device of FIG. 12, according to an embodiment of the present invention.

Referring to FIG. 13, the displaying device 1220 includes a recognizing unit 1221, an interfacing unit 1222, a processor 1223, and a display unit 1224.

The recognizing unit 1221 recognizes or identifies an object included in an image captured by a photographing unit (e.g., a camera) provided in the displaying device 1220. For example, when the displaying device 1220 captures an image of a scene including a baby, the recognizing unit 1221 may recognize that the baby is included in the obtained scene. Also, the recognizing unit 1221 may recognize or identify a person included in the captured image by using a face recognition algorithm.

The interfacing unit 1222 receives information of a visual metaphor representation or an image in which the visual metaphor representation is reflected from the apparatus 1100 (see FIG. 11). That is, the interfacing unit 1222 receives a processing result from the apparatus 1100.

The processor 1223 is hardware for controlling overall functions and operations of the displaying device 1220. The processor 1223 may process the information of the visual metaphor representation received from the apparatus 1100 and a recognition result received from the recognizing unit 1221 and may generate an image that is to be displayed on the display unit 1224. Alternatively, when the image in which the visual metaphor representation is reflected is received from the apparatus 1100, the processor 1223 may control the display unit 1224 to display the received image on the display unit 1224.

The display unit 1224, which is hardware for displaying a processing result obtained by the processor 1223, displays the image in which the visual metaphor representation is reflected.

Figure 14:
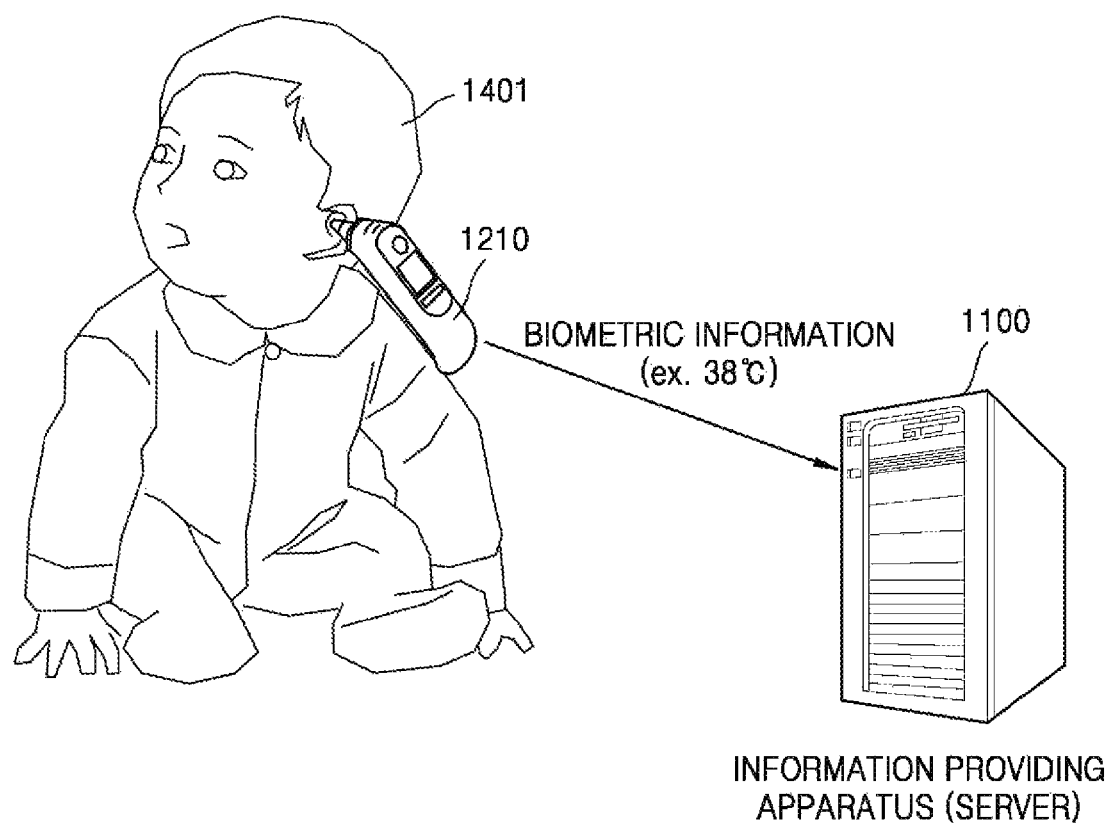
FIG. 14 is a view of a method performed by the apparatus of FIG. 12 to receive biometric information from the measuring device of FIG. 12, according to an embodiment of the present invention.

FIG. 14 is a view of a method performed by the apparatus of FIG. 12 to receive biometric information from the measuring device of FIG. 12 according to an embodiment of the present invention.

Referring to FIG. 14, the measuring device 1210 may measure biometric information (e.g., body temperature) of a baby 1401. The measuring device 1210 may transmit the measured biometric information (e.g., 38° C.) to the apparatus 1100.

The apparatus 1100 processes the received biometric information as information of a metaphor representation. For example, since a normal body temperature of a person is 36.5° C., the apparatus 1100 may determine that the measured biometric information (38° C.) exceeds a normal body temperature range. Accordingly, the apparatus 1100 may process the measured biometric information (38° C.) as a metaphor representation such as a flame. The metaphor representation may be modified to a size of a flame or a number of flames according to a degree of the measured body temperature, and may be modified to another representation other than a flame.

Figure 15:
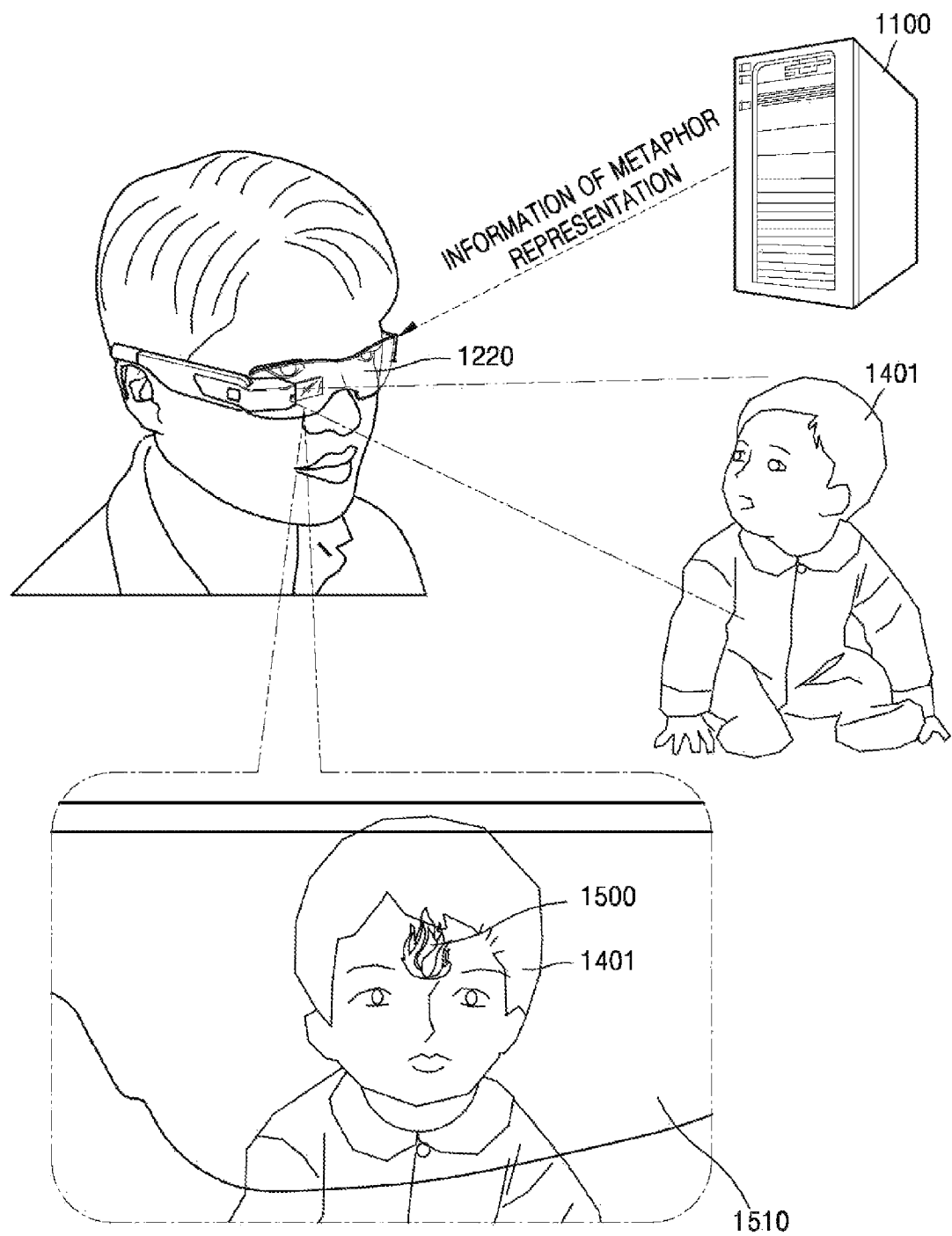
FIG. 15 is a view illustrating a case where a metaphor representation received from the apparatus of FIG. 12 is displayed on the displaying device of FIG. 12, according an embodiment of the present invention.

FIG. 15 is a view illustrating a case where a metaphor representation received from the apparatus of FIG. 12 is displayed on the displaying device of FIG. 12, according an embodiment of the present invention.

Referring to FIG. 15, it is assumed that the displaying device 1220 is an AR device.

The biometric information (38° C.) of the baby 1401 is processed as a metaphor representation 1500 such as a flame by the apparatus 1100. The apparatus 1100 transmits information of the metaphor representation 1500 to the displaying device 1220 (in particular, the interface 1222).

When a person wears the displaying device 1220 that is an AR device and watches the baby 1401, the displaying device 1220 (in particular, the recognizing unit 1221) recognizes the baby 1401. Next, the displaying device 1220 (in particular, the processor 1223) maps information about the recognized baby 1401 to the information of the metaphor representation 1500 received from the apparatus 1100. Accordingly, the metaphor representation 1500 indicating that the body temperature of the baby 1401 is higher than a normal body temperature overlaps the forehead of the baby 1401 on a display screen 1510. Accordingly, it may be easily recognized whether the biometric information of the baby 1401 is normal or abnormal.

Figure 16:
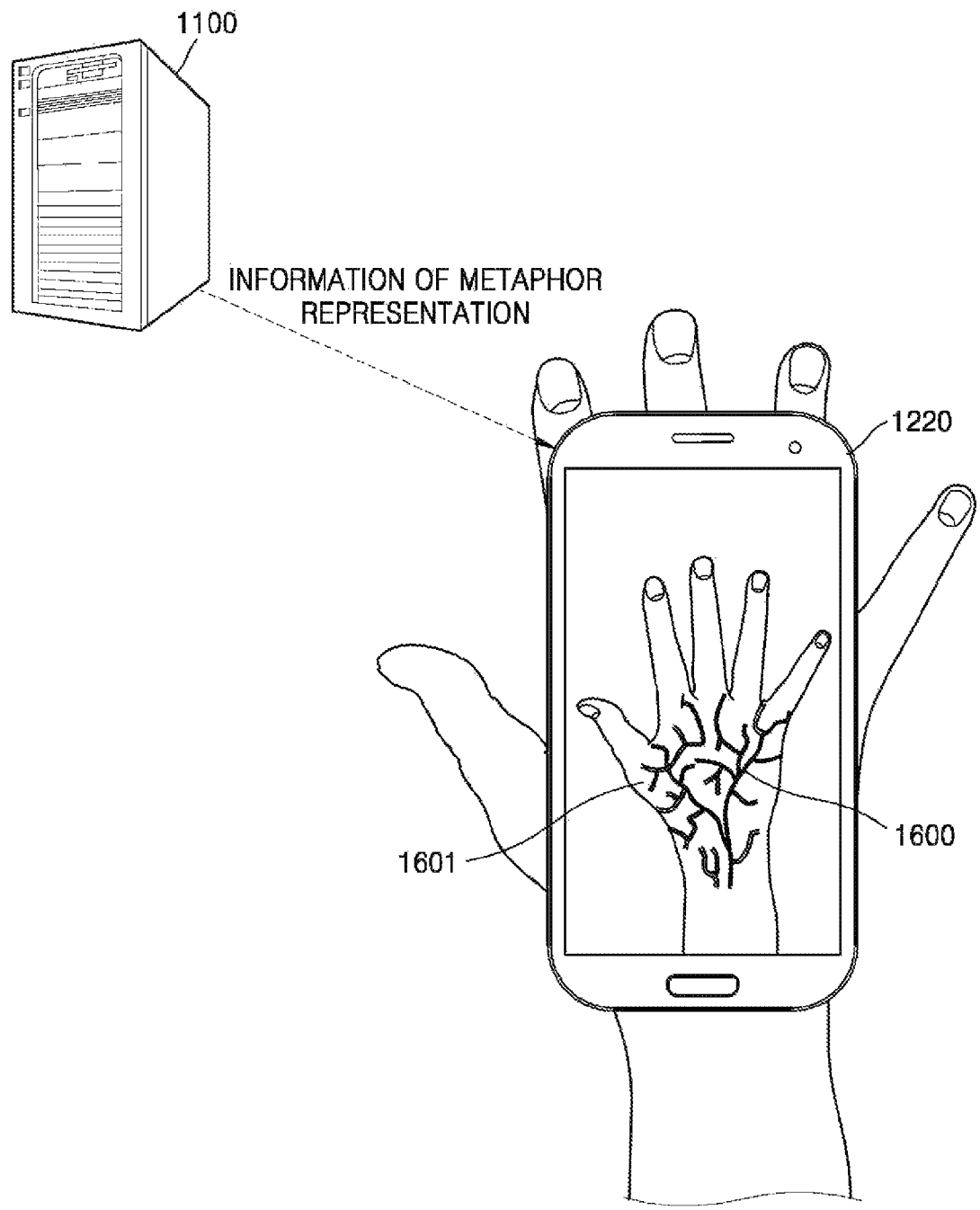
FIG. 16 is a view illustrating a case where a metaphor representation received from the apparatus of FIG. 12 is displayed on the displaying device of FIG. 12, according to another embodiment of the present invention.

FIG. 16 is a view illustrating a case where a metaphor representation received from the apparatus of FIG. 12 is displayed on the displaying device of FIG. 12, according to another embodiment of the present invention.

Referring to FIG. 16, it is assumed that the displaying device 1220 is a smart phone and that the measuring device 1210 may measure blood pressure by attaching a sensor to a hand of a user.

The measuring device 1210 may measure blood pressure of a user and may transmit the measured blood pressure to the apparatus 1100. The apparatus 1100 may process the blood pressure as a metaphor representation 1600 such as veins. When the blood pressure of the user is high, the apparatus 1100 may process the measured blood pressure as the metaphor representation 1600 that is expanded veins, and when the blood pressure of the user is normal, the apparatus 1100 may process the measured blood pressure as the metaphor representation 1600 that is normal veins.

The displaying device 1220 receives information of the metaphor representation 1600 from the apparatus 1100.

When the displaying device 1220 recognizes the hand of the user, the processed metaphor representation 1600 overlaps the back 1601 of the hand of the user on a display screen of the display unit 1224. The user may intuitively recognize a status of the blood pressure by checking whether the veins are expanded or not by using the metaphor representation 1600. That is, like in FIG. 4, a health condition may be easily identified through the displaying device 1220.

Figure 17:
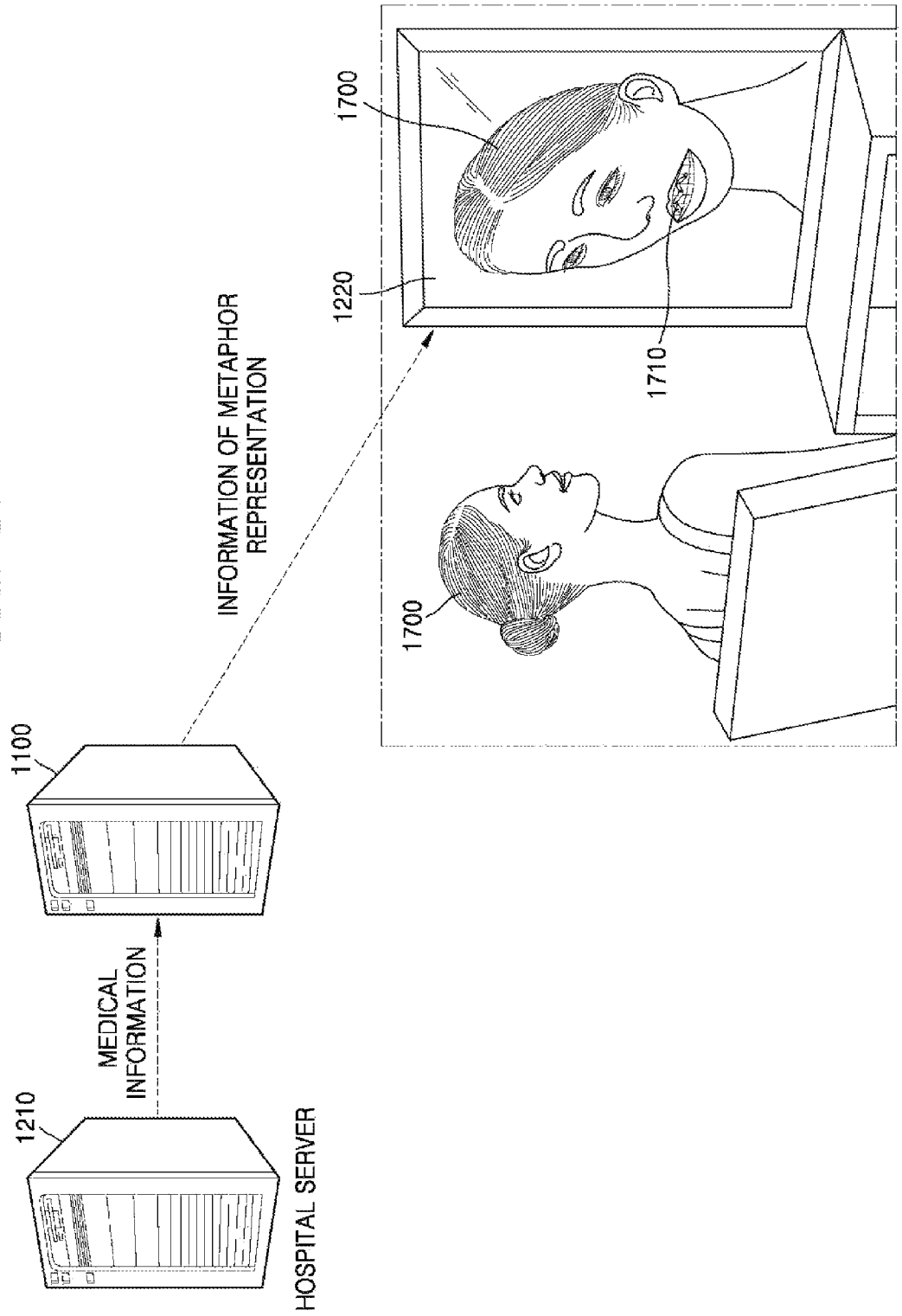
FIG. 17 is a view illustrating a case where a metaphor representation received from the apparatus of FIG. 12 is displayed on the displaying device of FIG. 12, according to another embodiment of the present invention.

FIG. 17 is a view illustrating a case where a metaphor representation received from the apparatus of FIG. 12 is displayed on the displaying device 1220 of FIG. 12, according to another embodiment of the present invention.

Referring to FIG. 17, it is assumed that the measuring device 1210 is a hospital server and the displaying device 1220 is a smart mirror.

The apparatus 1100 may receive teeth-related medical records of a user 1700 from the measuring device 1210. The apparatus 1100 may process a status of the teeth of the user 1700 as a metaphor representation 1710 such as a worm. The apparatus 1100 may process the status of the teeth as the metaphor representation 1710 that is a large worm or many worms.

The displaying device 1220 receives information of the metaphor representation 1710 from the apparatus 1100.

When the user 1700 is located in front of the displaying device 1220, the displaying device 1220 recognizes the user 1700. Next, the processed metaphor representation 1710 overlaps the teeth of the user 1700 on a display screen of the display unit 1224. The user 1700 may intuitively recognize whether the status of the teeth is healthy or unhealthy by using the metaphor representation 1710. That is, like in FIG. 5, a health condition may be easily identified through the displaying device 1220.

Figure 18:
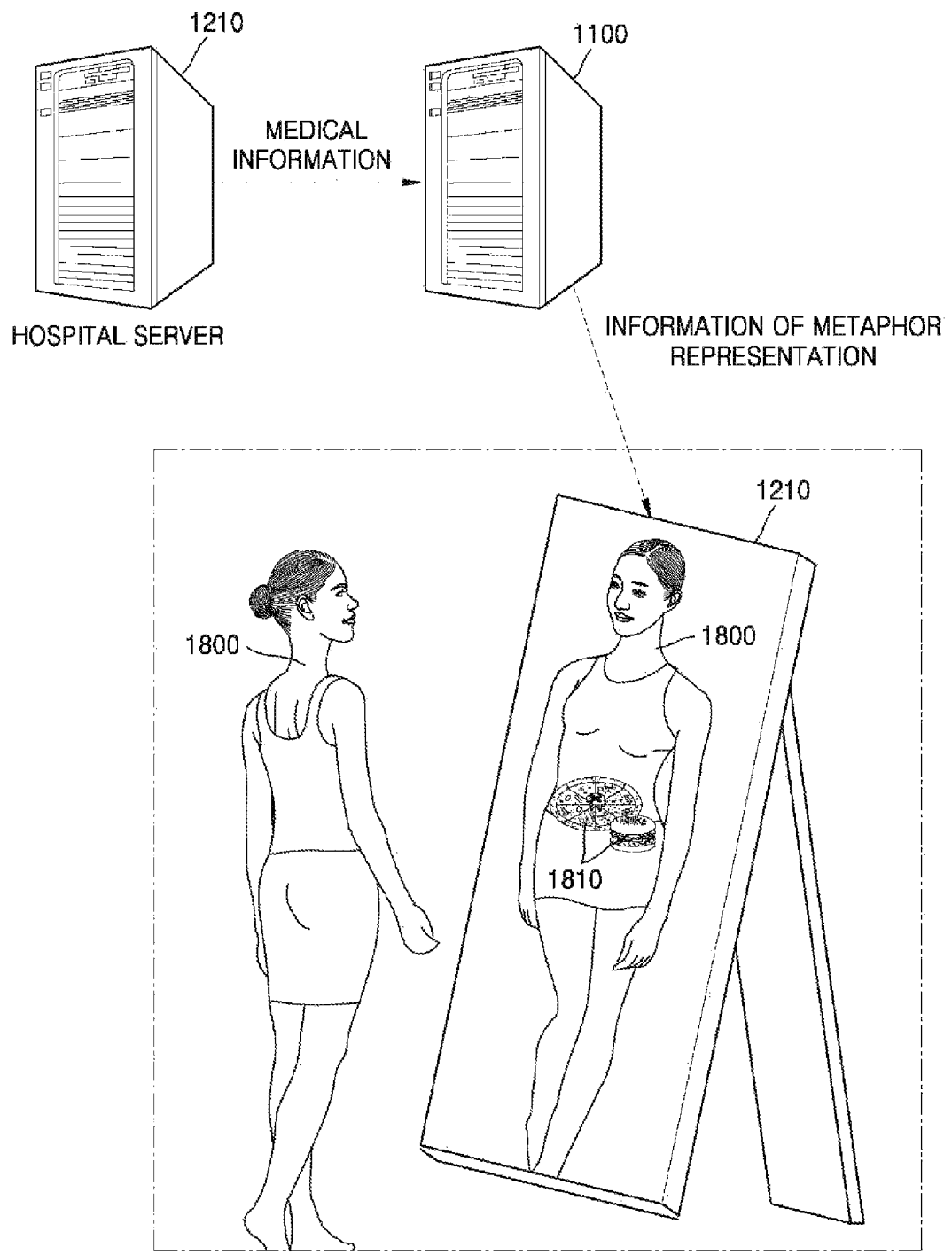
FIG. 18 is a view illustrating a case where a metaphor representation received from the apparatus of FIG. 12 is displayed on the displaying device of FIG. 12, according to anther embodiment of the present invention.

FIG. 18 is a view illustrating a case where a metaphor representation received from the apparatus of FIG. 12 is displayed on the displaying device of FIG. 12 according to anther embodiment of the present invention.

Referring to FIG. 18, it is assumed that the measuring device 1210 is a hospital server and the displaying device 1220 is a smart mirror.

The apparatus 1100 may receive obesity-related medical records of a user 1800 from the measuring device 1210. The apparatus 1100 may process a obesity level of the user 1800 as a metaphor representation 1810 such as fast food item, for example, a hamburger or pizza. The apparatus 1100 may process the obesity level as the metaphor representation 1810 that is more fast food items or more various fast food items as the obesity level worsens.

The displaying device 1220 receives information of the metaphor representation 1810 from the apparatus 1100.

When the user 1800 is located in front of the displaying device 1220, the displaying device 1220 recognizes the user 1800. Next, the processed metaphor representation 1810 overlaps the belly of the user 1800 on a display screen of the display unit 1224. The user 1800 may intuitively recognize whether the obesity level is high or not by using the metaphor representation 1810.

Figure 19:
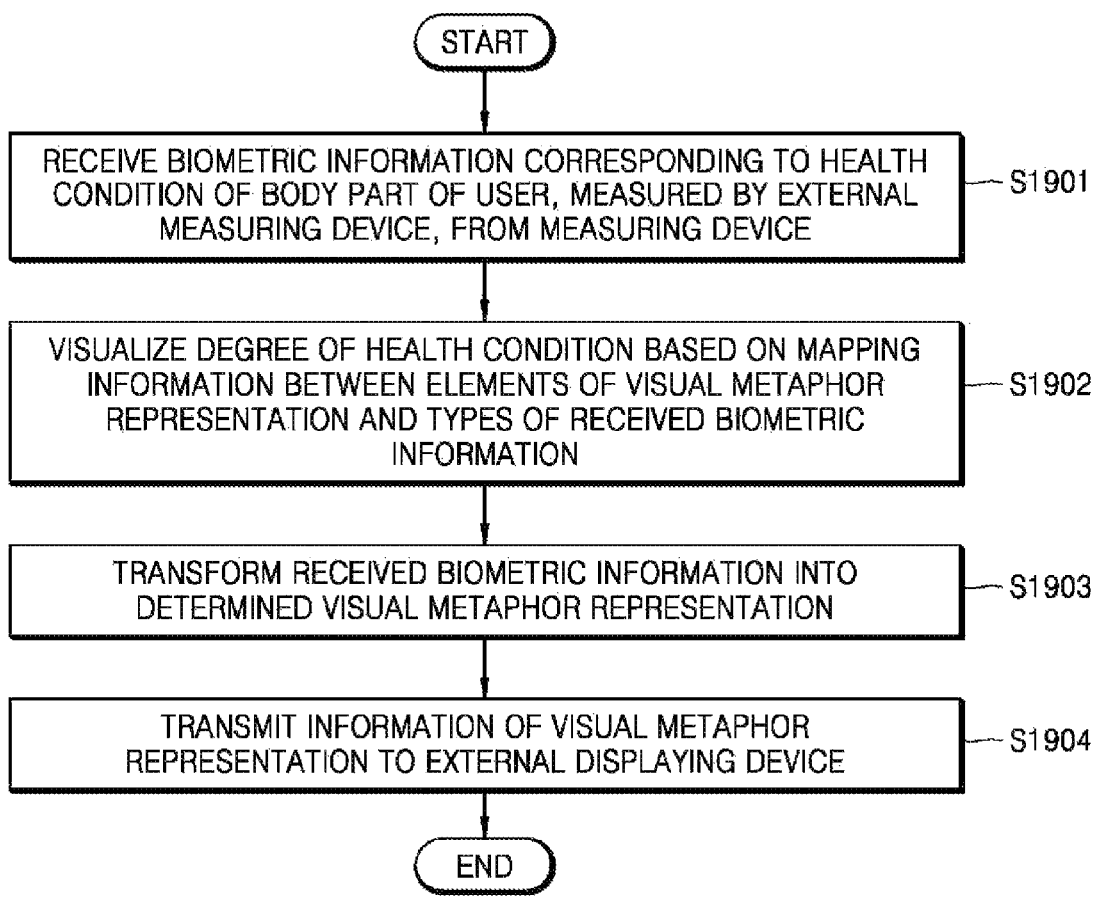
FIG. 19 is a flowchart of a method of providing information, according to another embodiment of the present invention.

FIG. 19 is a flowchart of a method of providing information, according to another embodiment of the present invention.

Referring to FIG. 19, the method includes steps sequentially performed by the apparatus 1100 or 2000 of FIGS. 11 through 22. Accordingly, descriptions already made above may apply to the method of FIG. 19.

In step S1901, the interfacing unit 1110 2010 receives biometric information corresponding to a health condition of a body part of a user, which is measured by the measuring device 1210 or 2050, from the measuring device 1210 or 2050.

In step 1902, the processor 1120 or 2020 determines a visual metaphor representation for characterizing a degree of the health condition based on mapping information between types of the received biometric information and components of the visual metaphor representation.

In step 1903, the processor 1120 or 2020 transforms the received biometric information into the determined visual metaphor representation.

In step 1904, the interfacing unit 1110 or 2010 transmits information of the visual metaphor representation to the displaying device 1220 or 2050.

Figure 20:
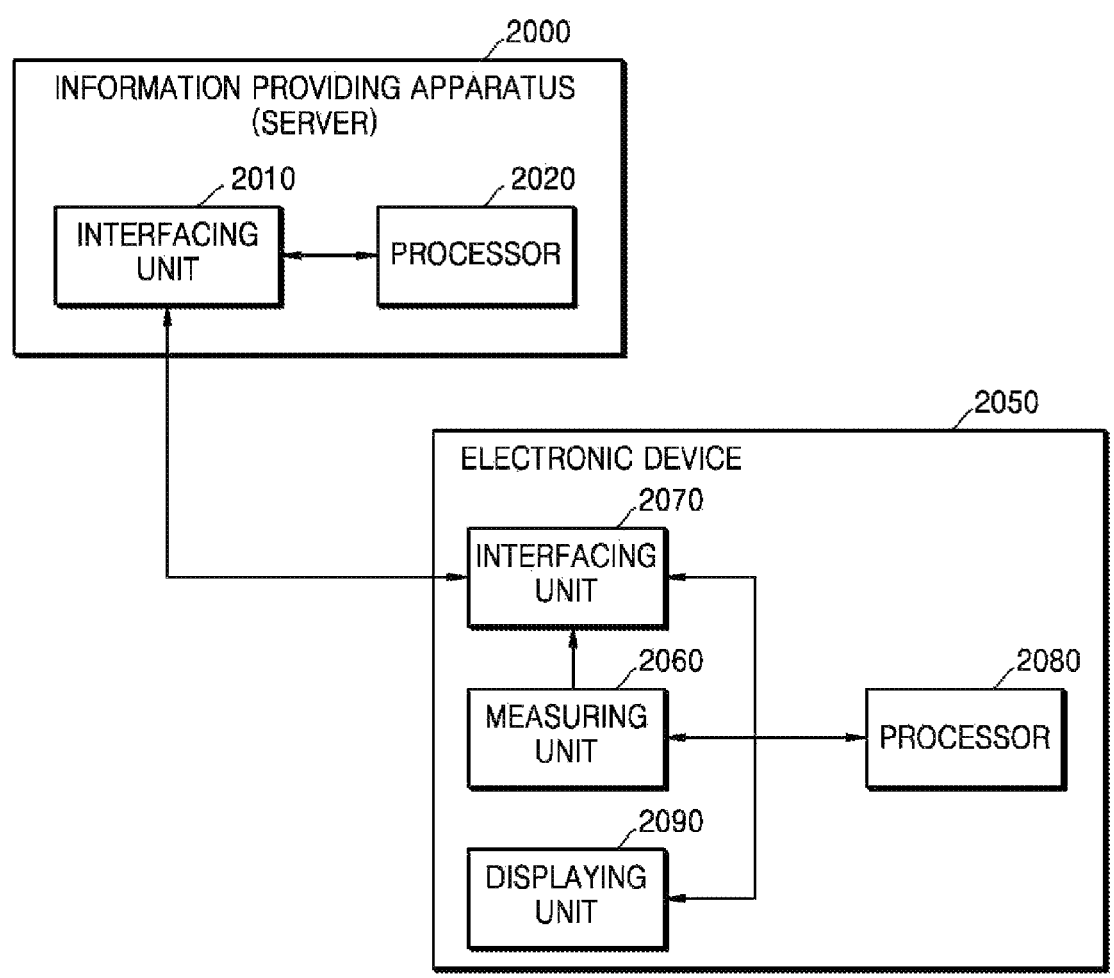
FIG. 20 is a block diagram of an apparatus for providing information and an electronic device, according to another embodiment of the present invention.

FIG. 20 is a block diagram of an apparatus for providing information and an electronic device, according to another embodiment of the present invention.

Referring to FIG. 20, the apparatus 2000 includes an interfacing unit 2010 and a processor 2020. That is, the apparatus 2000 does not include the measuring unit 110 and the display unit 130, unlike the apparatus 100 of FIG. 1 and the apparatus 700 of FIG. 7.

The electronic device 2050 includes a measuring unit 2060, an interfacing unit 2070, a processor 2080, and a display unit 2090. The electronic device 2050 may perform all of functions of the measuring unit 110 and the display unit 130 of the apparatus 100 of FIG. 1, or may perform all of functions of the measuring device 1210 and the displaying device 1220 of FIG. 12. The electronic device 2050 may correspond to a smart phone, a wearable device, an AR device, a VR device, or a smart mirror.

The interfacing unit 2010 of the apparatus 2000 receives biometric information, medical information, profile information, body part information, and user input information from the electronic device 2050. The interfacing unit 2010 corresponds to hardware configured to enable the apparatus 2000 to receive data from the electronic device 2050 or to transmit data to the electronic device 2050.

The processor 2020 corresponds to hardware configured to perform functions similar to those of the processor 120 of FIG. 1, the metaphor determining unit 710 and the processor 720 of FIG. 7, or the processor 1120 of FIGS. 11 and 12. Accordingly, the processor 2020 may perform the same operations as those of the processor 120, the metaphor determining unit 710, the processor 720, and the processor 1120. That is, the processor 2020 may process the biometric information as a metaphor representation by using the methods of FIGS. 1 through 10.

The processor 2020 processes the biometric information, the medical information, the profile information, the body part information, or the user input information received through the interfacing unit 2010. The processor 2020 may process the biometric information, the profile information, and the body part information to determine a visual metal representation, and may generate an image in which the determined visual metaphor representation is reflected. The interfacing unit 2010 may transmit information of the metaphor representation processed by the processor 2020 to the electronic device 2050.

The measuring unit 2060 of the electronic device 2050 measures the biometric information of the user. The biometric information may include any information related to the user's body. The measuring unit 2060 may further obtain information about a body part, the biometric information of which has been measured.

The interfacing unit 2070 of the electronic device 2050 transmits the biometric information measured by the measuring unit 2060 and the obtained information about the body part to the apparatus 2000 (in particular, the interfacing unit 2010). Also, the interfacing unit 2070 may transmit the profile information and the user input information to the apparatus 2000. Next, the interfacing unit 2070 of the electronic device 2050 receives the information of the metaphor representation processed by the processor 2020 of the apparatus 2000.

The processor 2080 of the electronic device 2050 is hardware for controlling overall functions and operations of the displaying device 2050. The processor 2080 may process the information of the metaphor representation received from the apparatus 2000 and may generate an image to be displayed on the display unit 2090. Alternatively, when the image in which the visual metaphor representation is reflected is received from the apparatus 2000, the processor 2080 may control the display unit 2090 to display the received image on the display unit 2090.

The display unit 2090, which is hardware for displaying a processing result obtained by the processor 2080, displays the image in which the visual metaphor representation is reflected.

Figure 21:
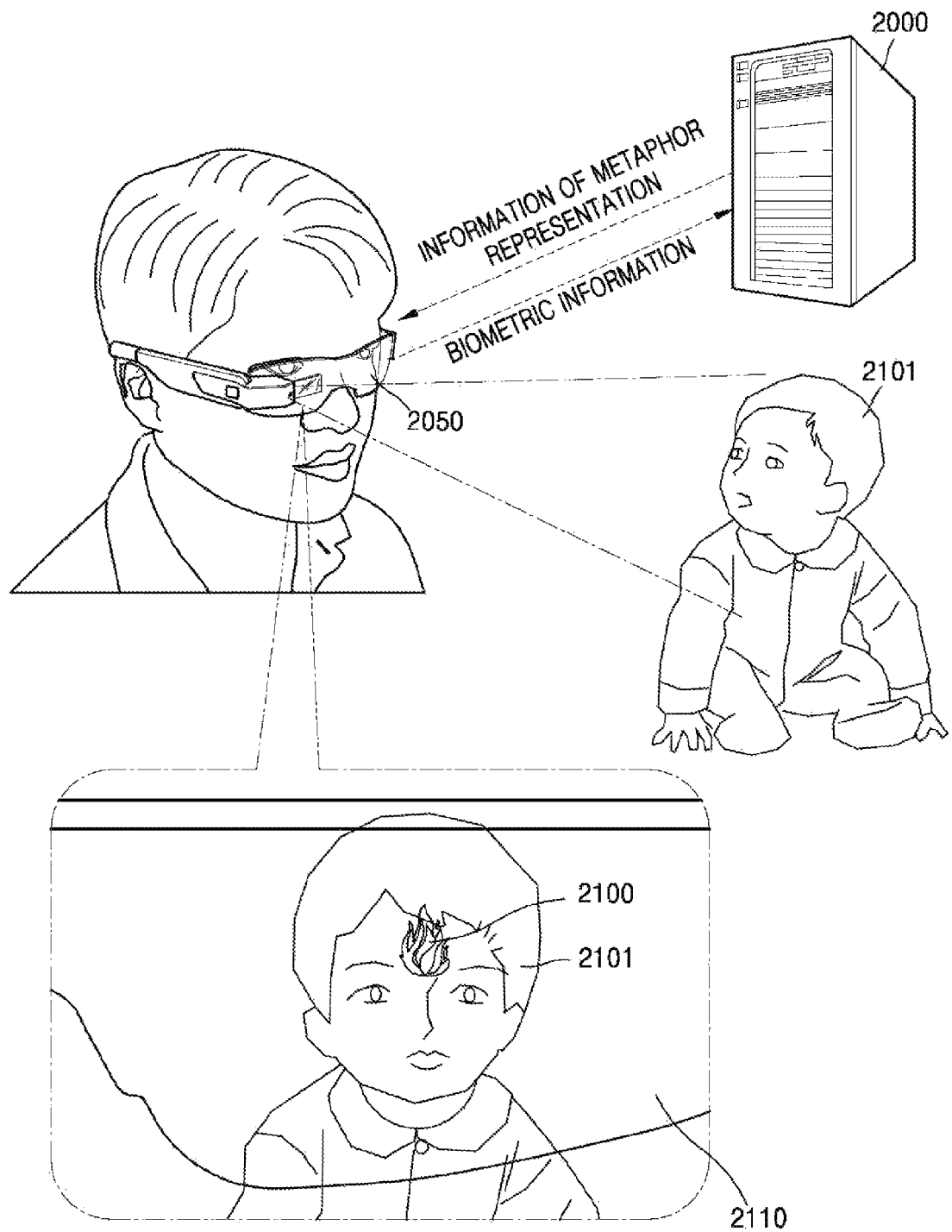
FIG. 21 is a view illustrating a case where the electronic device of FIG. 20 displays metaphor representation received from the apparatus of FIG. 20, according to an embodiment of the present invention.

FIG. 21 is a view illustrating a case where the electronic device of FIG. 20 displays a metaphor representation received from the apparatus of FIG. 20, according to an embodiment of the present invention.

Referring to FIG. 21, it will be assumed that the electronic device 2050 is an AR device.

The electronic device 2050 (in particular, the measuring unit 2060) may measure biometric information (e.g., a body temperature) of a baby 2101. The electronic device 2050 (in particular, the interfacing unit 2070) may transmit the measured biometric information (e.g., 38° C.) to the apparatus 2000.

The apparatus 2000 processes the received biometric information as information of a metaphor representation 2100. For example, since a normal body temperature of a person is 36.5° C., the apparatus 2000 may determine that the measured body temperature (38° C.) exceeds a normal body temperature range. Accordingly, the apparatus 2000 may process the measured body temperature (38° C.) as the metaphor representation 2100 such as a flame. The metaphor representation 2100 may be modified in various ways to a size of a flame or a number of flames according to a degree of the measured body temperature, or may be modified to another representation other than a flame.

The apparatus 2000 transmits information of the metaphor representation 2100 to the electronic device 2050.

When a person wears the electronic device 2050 (that is, an AR device) and watches the baby 2101, the electronic device 2050 (in particular, the processor 2080) maps information of the baby 2101 to the information of the metaphor representation 2100 received from the apparatus 2000. Accordingly, the metaphor representation 2100, indicating that the body temperature of the baby 2101 is higher than a normal body temperature, overlaps the forehead of the baby 2101 on a display screen 2110 of the electronic device 2050 (in particular, the display unit 2090). Accordingly, the user may easily recognize whether the biometric information of the baby 2101 is normal or abnormal.

Figure 22:
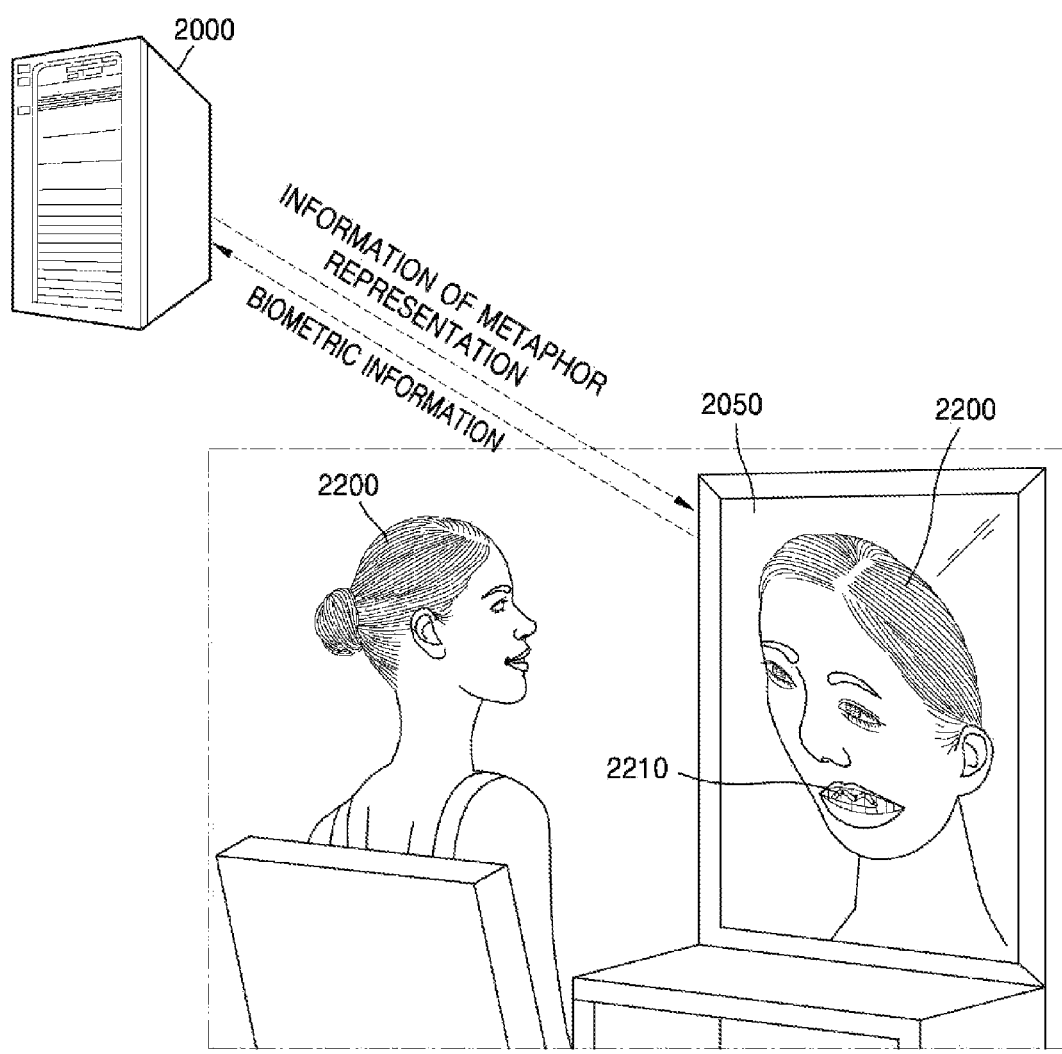
FIG. 22 is a view illustrating a case where a metaphor representation processed by the apparatus of FIG. 20 is displayed on the electronic device of FIG. 20, according to another embodiment of the present invention.

FIG. 22 is a view illustrating a case where a metaphor representation processed by the apparatus of FIG. 20 is displayed on the electronic device of FIG. 20, according to another embodiment of the present invention.

Referring to FIG. 22, it will be assumed that the electronic device 2050 is a smart mirror.

When a user 2200 is located in front of the electronic device 2050 and shows the teeth, the electronic device 2050 (in particular, the measuring unit 2060) may measure a status of the teeth of the user 2200. The electronic device 2050 (in particular, the interfacing unit 2070) may transmit information of the measured status of the teeth to the apparatus 2000.

The apparatus 2000 processes the received information of the status of the teeth as information of a metaphor representation 2210. The apparatus 2000 may process the status of the teeth of the user 2200 as the metaphor representation 2210 such as a worm. The apparatus 2200 may process the status of the teeth as the metaphor representation 2210 that is a large worm or many worms.

The electronic device 2050 receives the information of the metaphor representation 2210 from the apparatus 2000.

The processed metaphor representation 2210 overlaps the teeth of the user 2200 on a display screen of the electronic device 2050. The user 2200 may intuitively recognize whether the status of the teeth is healthy or unhealthy by using the metaphor representation 2210. That is, like in FIG. 5, a health condition may be easily identified through the electronic device 2050.

Various embodiments of the present invention may be implemented through computer programs executed in general-use digital computers using a computer readable recording medium. Examples of computer readable recording mediums include magnetic storage media (e.g., Read Only Memory (ROM), floppy disks, hard disks, etc.), optical recording media (e.g., Compact Disc (CD)-ROMs, or Digital Versatile Discs (DVDs)), etc.

While this invention has been particularly shown and described with reference to embodiments thereof, it will be understood by those skilled in the art that various changes in form and details may be made therein without departing from the spirit and scope of the invention as defined by the appended claims. Embodiments should be considered in descriptive sense only and not for purposes of limitation. Accordingly, the scope of the invention is defined not by the detailed description of the invention but by the appended claims, and all differences within the scope of the claims will be construed as being included in the present invention.

What is claimed is:

1. An apparatus for providing information, the apparatus comprising:
    an interfacing unit configured to receive biometric information, which is measured by an external measuring device, corresponding to a health condition of a body part of a user, from the external measuring device; and
    a processor configured to determine a visual metaphor representation for characterizing a degree of the health condition based on mapping information between components of the visual metaphor representation and types of the received biometric information, and transform the received biometric information into the determined visual metaphor representation,
wherein the interfacing unit is further configured to transmit the transformed visual metaphor representation to an external displaying device.

2. The apparatus of claim 1, wherein the processor is further configured to generate an image in which the visual metaphor representation is reflected on an object visualizing the body part to identify the health condition.

3. The apparatus of claim 1, wherein the processor is further configured to process the biometric information based on profile information of the user.

4. The apparatus of claim 1, wherein the interfacing unit is further configured to receive a photographed image of the body part from the external measuring device connected through a network.

5. The apparatus of claim 1, wherein the biometric information includes one of electrocardiogram information, electroencephalogram information, stress level information, bone mineral density information, body mass index information, calories burned information, and physical age information.

6. A method for providing information at information providing apparatus, the method comprising:
receiving biometric information, which is measured by an external measuring device, corresponding to a health condition of a body part of a user, from the external measuring device;
determining a visual metaphor representation for characterizing a degree of the health condition based on mapping information between components of the visual metaphor representation and types of the received biometric information;
transforming the received biometric information into the determined visual metaphor representation; and
transmitting the transformed visual metaphor representation to an external displaying device.

7. The method of claim 6, wherein further comprising generating an image in which the visual metaphor representation is reflected on an object visualizing the body part to identify the health condition.

8. The method of claim 6, wherein further comprising processing the biometric information based on profile information of the user.

9. The method of claim 6, wherein further comprising receiving a photographed image of the body part from the external measuring device connected through a network.

10. The method of claim 6, wherein the biometric information includes one of electrocardiogram information, electroencephalogram information, stress level information, bone mineral density information, body mass index information, calories burned information, and physical age information.

* * * * *